United States Patent [19]

Lunn et al.

[11] 4,382,932
[45] May 10, 1983

[54] ISOQUINOLINIUM SUBSTITUTED CEPHALOSPORINS

[75] Inventors: William H. W. Lunn; William J. Wheeler, both of Indianapolis, Ind.

[73] Assignee: Eli Lilly and Company, Indianapolis, Ind.

[21] Appl. No.: 300,142

[22] Filed: Sep. 8, 1981

[51] Int. Cl.³ .................. A61K 31/545; C07D 501/46
[52] U.S. Cl. ...................... 424/246; 544/22; 544/27; 544/28; 548/133; 548/233; 548/245
[58] Field of Search ................ 424/246; 544/22, 27

[56] References Cited

U.S. PATENT DOCUMENTS

| | | | |
|---|---|---|---|
| 3,960,849 | 6/1976 | Breuer | 260/243 C |
| 4,024,133 | 5/1977 | Cook et al. | 544/27 |
| 4,258,041 | 3/1981 | O'Callaghan et al. | 424/246 |
| 4,278,793 | 7/1981 | Durckheimer et al. | 544/27 |

OTHER PUBLICATIONS

Derwent Abstract No. 32890.

Primary Examiner—Paul M. Coughlan, Jr.
Attorney, Agent, or Firm—William B. Scanlon; Arthur R. Whale

[57] ABSTRACT

Broad spectrum cephalosporin antibiotics represented by the formula

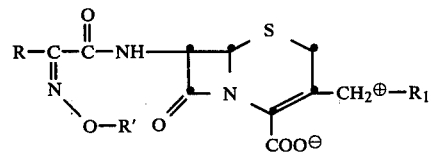

wherein R is a 3-aminoisoxazol-5-yl, 2-aminooxazol-4-yl, or a 5-amino-1,2,4-oxadiazol-3-yl group; $R_1$ is isoquinolinium or substituted isoquinolinium; and R' is $C_1$-$C_4$ alkyl, an N-substituted carbamoyl group, or a carboxy-substituted alkyl or cycloalkyl group; and the pharmaceutically acceptable non-toxic salts thereof; are prepared by the reaction of a 3-iodomethyl cephalosporin, having the above 2-(amino-substituted heterocyclic)-2-oximinoacetyl side chain, with isoquinoline or a substituted isoquinoline. Pharmaceutical formulations of the antibiotics and a method for treating bacterial infections with the antibiotics are provided.

13 Claims, No Drawings

ISOQUINOLINIUM SUBSTITUTED CEPHALOSPORINS

BACKGROUND OF THE INVENTION

This invention relates to cephalosporin antibiotics. In particular, it relates to cephalosporin antibiotic compounds substituted in the 3'-position with a isoquinolinium or substituted isoquinolinium group, and in the 7-position with a 2-(aminooxazolyl or aminooxadiazolyl)-2-oximinoacetyl group.

Cephalosporin compounds substituted in the 3'-position with a quaternary ammonium group have been known for some time. For example, cephalosporin $C_A$ (pyridine) was one of the first derivatives of cephalosporin C prepared by Abraham et al. following the discovery of cephalosporin C, Hale, Newton, and Abraham, *Biochem. J.*, 79, 403 (1961).

Cephaloridine, the well-known clinical antibiotic, is the 3'-pyridinium cephalosporin, 7-(α-thienylacetamido)-3-(pyridinium-1-ylmethyl)-3-cephem-4-carboxylate. Recently, Heymes et al., U.S. Pat. No. 4,152,432, describe semi-synthetic cephalosporin antibiotics wherein the 7-position side chain is a 7-[2-(2-(aminothiazol-4-yl)-2-alkoxyiminoacetamido] group and the 3-position substituent is acetoxymethyl. More recently, Takeda, U.K. Patent Specification No. 1,581,854, describes syn-7-[2-(2-aminothiazol-4-yl)-2-methoxyimino]-3-pyridiniummethyl-3-cephem-4-carboxylate. O'Callaghan, et al., in U.S. Pat. No. 4,258,041, describe 7-[2-(2-aminothiazole-4-yl)-2-oximinoacetamido]-3-(pyridinium-1-ylmethyl)-3-cephem-4-carboxylate antibiotics, and the corresponding compounds wherein the pyridinium group in the 3'-position is substituted with a carbamoyl group.

Because of the continuing need for improved antibiotic therapy in clinical practice, the search continues for broad spectrum antibiotics with greater potency and minimal toxicity. The semi-synthetic cephalosporin antibiotics long have been recognized as broad spectrum antibiotics, and several have achieved clinical importance. Continued research with the cephalosporin antibiotics has centered of late with the development of antibiotics having higher activity against certain gram-negative microorganisms such as pseudomonas and those which produce β-lactamases destructive of β-lactam antibiotics.

SUMMARY OF THE INVENTION

Broad spectrum cephalosporin antibiotics represented by the following formula

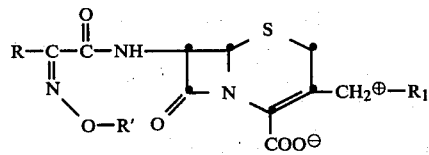

are provided by this invention. In the above formula, R represents an amino-substituted oxazole, oxadiazole, or isoxazole ring, R' represents hydrogen, $C_1-C_4$ alkyl, an N-substituted carbamoyl group, or a carboxy or carboxamido-substituted alkyl or cycloalkyl group, and $R_1$ is isoquinolinium or substituted isoquinolinium substituted by alkyl, halogen, amino, hydroxy, etc. The antibiotics can be prepared by reacting a 3-acetoxymethyl or 3-halomethyl cephalosporin having the same 7-position side chain as a compound of the above formula with isoquinoline or a substituted isoquinoline. Alternatively, the compounds are prepared by the N-acylation of a 7-amino-3-isoquinolinium or substituted isoquinolinium cephalosporin. Preferably, the compounds are obtained by the reaction of a 3-iodomethyl cephalosporin with isoquinoline or a substituted isoquinoline.

The invention also provides pharmaceutical formulations comprising the antibiotic of the above formula as well as a method for treating bacterial infections comprising the use of the antibiotic.

DETAILED DESCRIPTION

The cephalosporin compounds provided by this invention are represented by the following formula I

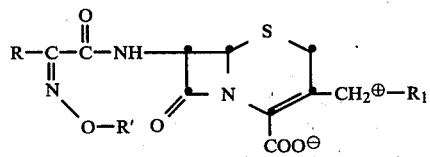

wherein R is an amino-substituted heterocyclic of the formula

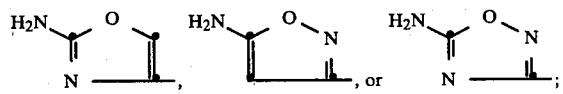

R' is hydrogen, $C_1-C_4$ alkyl, a carboxy-substituted alkyl or a carboxy-substituted cycloalkyl group represented by the formula

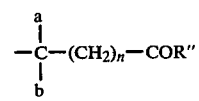

wherein a and b when taken separately are independently hydrogen or $C_1-C_3$ alkyl, and a and b when taken together with the carbon atom to which they are bonded form a $C_3-C_7$ carbocyclic ring; n is 0–3; and R'' is hydroxy, $C_1-C_4$ alkoxy, or amino; or R' is a substituted carbamoyl group represented by the formula

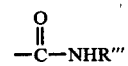

wherein R''' is $C_1-C_4$ alkyl, phenyl or $C_1-C_3$ alkyl substituted by phenyl; $R_1$ is isoquinolinium or substituted isoquinolinium, substituted by amino, $C_1-C_4$ alkylamino, di-($C_1-C_4$ alkyl) amino, hydroxy, $C_1-C_4$ alkoxy, halogen, $C_1-C_4$ alkyl, cyano, trifluoromethyl, sulfo (—$SO_3H$), aminosulfonyl (—$SO_2NH_2$), carboxy, $C_1-C_4$ alkoxycarbonyl, hydroxy substituted $C_1-C_3$ alkyl, formyl, $C_2-C_4$ alkanoyl, thiocarbamoyl, or carbamoyl; and the pharmaceutically acceptable non-toxic salts thereof.

The terms employed in the definition of the compounds represented by formula 1 have the following meanings. "$C_1-C_4$ alkyl" refers to the straight and branched chained alkyl hydrocarbon chains such as methyl, ethyl, n-propyl, iso-propyl, n-butyl, t-butyl, and the like; "$C_1-C_4$ alkoxy" refers to methoxy, ethoxy, n-propoxy, isopropoxy, n-butoxy, t-butoxy, and the like;

"halogen" refers to fluoro, chloro, or bromo; "$C_1$–$C_4$ alkylamino" refers to methylamino, ethylamino, n-propylamino, isopropylamino, n-butylamino, isobutylamino, and the like; and "di($C_1$–$C_4$ alkyl)amino" refers to dimethylamino, diethylamino, di-(n-propyl)amino, di-(n-butyl)amino, and the like; "$C_1$–$C_4$ alkoxycarbonyl" refers to methoxycarbonyl, ethoxycarbonyl, isopropoxycarbonyl, t-butyloxycarbonyl, and the like; "hydroxy substituted $C_1$–$C_3$ alkyl" refers to hydroxymethyl, 2-hydroxyethyl, 1-hydroxyethyl, 3-hydroxypropyl, 2-hydroxypropyl, and the like; and "$C_2$–$C_4$ alkanoyl" refers to acetyl, propionyl, butyryl, iso-butyryl, and the like.

As described above, the compounds of the invention have a quaternary isoquinolinium group in the 3'-position as represented by the term "$R_1$". As such, the compounds are also referred to as cephalosporin betaines characterized by the $C_4$ carboxylate anion and the quaternary isoquinolinium group in the 3'-position. Illustrative of these 3'-isoquinolinium groups are the amino-substituted isoquinolinium groups such as 4-aminoisoquinolinium, 5-aminoisoquinolinium, 7-aminoisoquinolinium, and like groups; the $C_1$–$C_4$ alkylamino-substituted isoquinolinium groups such as 4-methylaminoisoquinolinium, 5-ethylaminoisoquinolinium, 6-methylaminoisoquinolinium, 4-(n-butyl)aminoisoquinolinium, 5-isopropylaminoisoquinolinium, 7-methylaminoisoquinolinium, and the like; the di($C_1$–$C_4$ alkyl)amino-substituted isoquinolinium groups such as 4-dimethylaminoisoquinolinium, 4-diethylaminoisoquinolinium, 5-dimethylaminoisoquinolinium, 6-dimethylaminoisoquinolinium, 4-di-(n-butyl)aminoisoquinolinium, 7-di-(n-propyl)aminoisoquinolinium, and the like; the hydroxy-substituted isoquinolinium groups such as 4-hydroxyisoquinolinium, 5-hydroxyisoquinolinium, 7-hydroxyisoquinolinium, 8-hydroxyisoquinolinium, and the like; isoquinolinium groups substituted by the sulfonic acid group (sulfo) such as isoquinolinium-5-sulfonic acid, isoquinolinium-6-sulfonic acid, isoquinolinium-4-sulfonic acid, and the like; the aminosulfonyl-substituted isoquinolinium groups such as isoquinolinium-5-sulfonamide, isoquinolinium-4-sulfonamide, and the like; the carbamoyl and thiocarbamoyl-substituted isoquinolinium groups such as 5-carbamoylisoquinolinium, 4-carbamoylisoquinolinium, 4-thiocarbamoylisoquinolinium, 6-carbamoylisoquinolinium, and the like; the lower alkyl-substituted isoquinolinium groups such as 8-methylisoquinolinium, 3-methylisoquinolinium, 4-ethylisoquinolinium, 5-methylisoquinolinium, 1,5-dimethylisoquinolinium, and the like; the halo-substituted isoquinolinium groups such as 5-chloroisoquinolinium, 5-bromoisoquinolinium, 5-fluoroisoquinolinium, 6-chloroisoquinolinium, 7-fluoroisoquinolinium, and like halogen-substituted isoquinolinium groups; the carboxy-substituted isoquinolinium groups such as 4-carboxyisoquinolinium, 5-carboxyisoquinolinium, 7-carboxyisoquinolinium, and the like; the $C_1$–$C_4$ alkoxycarbonyl-substituted isoquinolinium groups, such as 4-methoxycarbonylisoquinolinium, 5-ethoxycarbonylisoquinolinium, 7-t-butyloxycarbonylisoquinolinium, and the like; the $C_1$–$C_4$ alkoxy-substituted isoquinolinium groups such as 4-methoxyisoquinolinium, 4-isopropoxyisoquinolinium, 5-ethoxyisoquinolinium, 6-t-butyloxyisoquinolinium, 7-methoxyisoquinolinium, and the like; the cyanoisoquinolinium groups such as 4-cyanoisoquinolinium, 5-cyanoisoquinolinium, 7-cyanoisoquinolinium, and the like; the hydroxyalkyl substituted isoquinolinium groups such as 5-hydroxymethylisoquinolinium, 5-hydroxyethylisoquinolinium, 4-(3-hydroxypropyl)isoquinolinium, 6-(2-hydroxypropyl)isoquinolinium, and the like; the $C_2$–$C_4$ alkanoyl substituted isoquinolinium groups such as 5-acetylisoquinolinium, 4-propionylisoquinolinium, 7-butyrylisoquinolinium, 6-acetylisoquinolinium, and the like; and the trifluoromethyl-substituted isoquinolinium groups such as 4-trifluoromethylisoquinolinium, 6-trifluoromethylisoquinolinium, 5-trifluoromethylisoquinolinium, and like groups.

When in the above formula 1, R" is hydroxy, the carboxy group of the carboxy-substituted alkyl or carboxy-substituted cycloalkyl group can be protected with a carboxy-protecting group during the synthesis of such compounds of formula 1. Carboxy-protecting groups which are suitable include the well-known carboxy-protecting groups useful for the temporary protection of the $C_4$ carboxy group of the cephalosporin antibiotics. Such groups are, for example, benzyl and substituted benzyl, for example, p-methoxybenzyl, p-nitrobenzyl, diphenylmethyl (benzhydryl), 4-methoxydiphenylmethyl, 4,4'-diphenylmethyl, t-butyl, the halo-substituted alkyl-protecting groups such as 2-iodoethyl, 2,2,2-trichloroethyl, 2,2,2-tribromoethyl, and like carboxy-protecting groups.

The compounds of the invention form acid addition salts. Salts formed with such acids as hydrochloric acid, hydrobromic acid, sulfuric acid, and phosphoric acid can be prepared and are included in this invention. Likewise, salts with the strong organic acids such as the sulfonic acids, for example, methanesulfonic acid, benzenesulfonic acid, and toluenesulfonic acid are suitable acid addition salts.

Examples of the carboxy-substituted alkyl and carboxy-substituted cycloalkyl groups represented by the term "R''" are carboxymethyl, carboxyethyl, carboxypropyl, 2-carboxypropyl, 2-carboxybutyl, 3-carboxypentyl, 1-carboxycyclobutan-1-yl, 1-carboxycyclopentan-1-yl, 1-carboxycyclohexan-1-yl, and the like, as well as the carboxy-protected and $C_1$–$C_4$ alkyl ester derivatives thereof.

Examples of substituted carbamoyl groups represented by R' include N-methylcarbamoyl, N-ethylcarbamoyl, N-isopropylcarbamoyl, N-n-butylcarbamoyl, N-phenylcarbamoyl, N-benzylcarbamoyl, N-(2-phenylethyl)carbamoyl, N-(3-phenylpropyl)carbamoyl, N-(2-phenylpropyl)carbamoyl, and the like.

The 7-acylamino-3'-isoquinolinium compounds of the invention are illustrated by the following structural formula wherein $R_2$ represents the substitutent group of the substituted isoquinolinium as defined above.

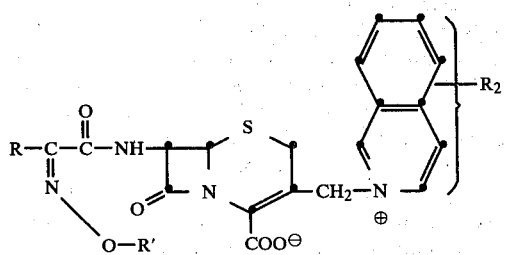

As is shown by the above formula, the substituent $R_2$ can be located on either ring of the isoquinolinium group. The term R represents the amino-substituted oxazole, isooxazole, or oxadiazole ring.

The compounds of the invention are prepared with the corresponding 7-acylamino-3-acetoxymethylcephalosporin by converting the 3-acetoxymethyl group thereof to a 3-halomethyl derivative, and thereafter reacting the 3-halomethyl derivative with the isoquinoline or substituted isoquinoline to obtain a compound of the invention. The method of preparation is illustrated by the following reaction scheme in which isoquinoline is used.

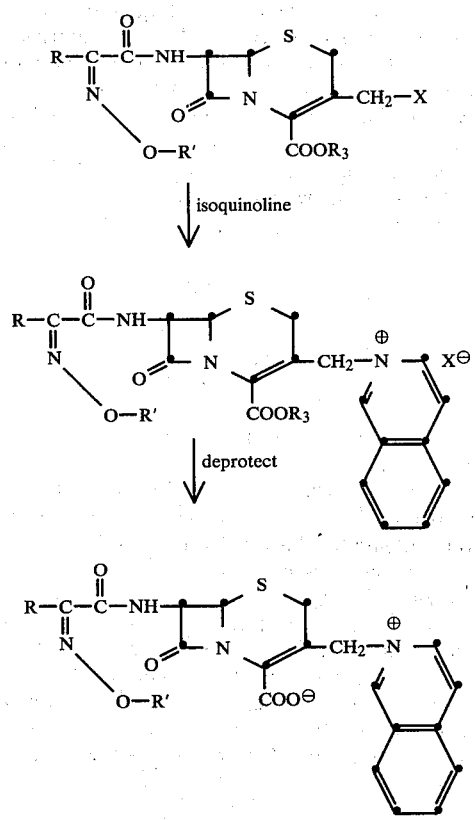

In the above formulas, R and R' have the same meanings as defined hereinabove, X is chloro, bromo, or iodo, and $R_3$ is a carboxy-protecting group. The amino group of the amino-substituted oxazole or isoxazole ring R may also be protected during the reaction. The amino group can be protected suitably by trityl or an alkoxycarbonyl protecting group such as t-butyloxycarbonyl, or t-amyloxycarbonyl, or an arylalkoxycarbonyl group such as benzyloxycarbonyl or p-nitrobenzyloxycarbonyl; or preferably by a silyl protecting group such as a trialkylsilyl group, eg. trimethylsilyl. The amino group of the 5-amino-1,2,4-oxadiazole ring need not be protected due to its low basicity.

The carboxy-protecting group $R_3$ is preferably a readily removable ester function conventionally used for the temporary protection of the $C_4$ carboxy group of the caphalosporins. Examples of these ester groups are recited hereinabove for the term R''. Silyl esters such as the trimethylsilyl ester are preferred.

The preferred method for preparing the compounds of the invention comprises the use of a 7-acylamino-3-iodomethyl derivative wherein the carboxy and amino groups are protected by silylation such as with a lower trialkylsilyl group, preferably trimethylsilyl. In carrying out the preparation of a compound of the invention by the preferred method, the 7-acylamino-3-acetoxymethyl-4-carboxylic acid is first silylated to block the reactive carboxyl and amino functional groups present in the molecule. The silylation is carried out with one of the commonly employed silylating agents, for example, mono- or bis-trimethylsilylacetamide or, preferably, with mono- or bis-trimethylsilyltrifluoroacetamide. The silylation is carried out in an inert solvent such as a halogenated hydrocarbon solvent, for example, methylene chloride, chloroform, chloroethane, or other inert organic solvent such as acetonitrile or propionitrile. The silylated derivative is then allowed to react with trimethylsilyliodide (TMSI) to form the corresponding 3-iodomethyl silylated derivative. The reaction mixture containing the silylated 3-iodomethyl derivative is evaporated to remove the solvent, and the concentrate is dissolved in acetonitrile and is treated with a slight excess of tetrahydrofuran to degrade any excess TMSI remaining. To this solution is then added isoquinoline or the substituted derivative thereof to form a compound of formula 1 as the silylated derivative. Upon the addition of water, the silyl derivatives are hydrolyzed to form a compound of the invention.

The following reaction scheme, wherein isoquinoline or a substituted isoquinoline is employed as an example, illustrates the preparation of the compounds of the invention.

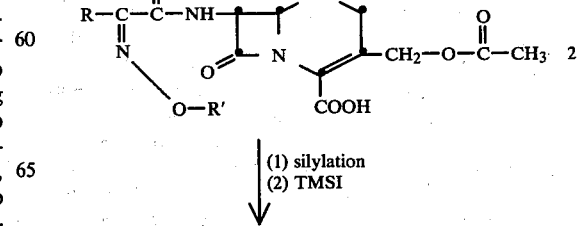

(1) silylation
(2) TMSI

-continued

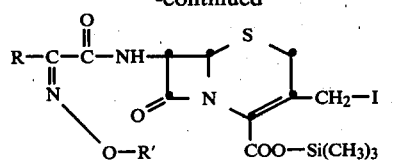

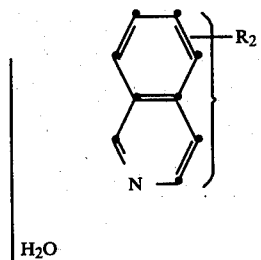

↓ H₂O

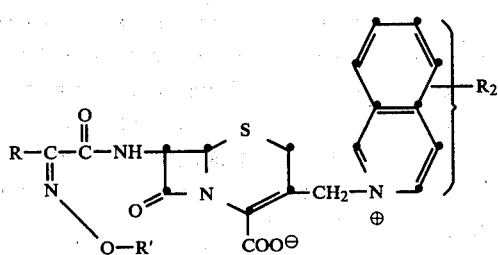

The preparation of the 3-iodomethylcephalosporin intermediate is carried out according to the process described by Bonjouklian in U.S. Pat. No. 4,266,049, issued May 8, 1981. In carrying out the preparation of the 3-iodomethylcephalosporin, other trialkylsilyl iodides may be employed as described by Bonjouklian. Trimethylsilyl iodide is the preferred reagent and is used to illustrate the preparation of the compounds herein.

Compounds represented by the formula 2 which have groups reactive toward the trialkylsilyliodide are protected by silylation prior to reaction with silyliodide. For example, when in formula 2 R' is hydrogen, a carboxy-substituted alkyl or carboxy-substituted cycloalkyl group and R" is OH, the free oxime hydroxy group and the free carboxylic acid functions are blocked from reaction with the silyl iodide by first silylating the starting material with a silylating agent such as N-methyl-N-trimethylsilyltrifluoroacetamide (BSTFA) or other suitable silylating reagent. Likewise, the amino-group of the amino-substituted heterocyclic ring in the 7-position side chain is protected by silylation unless already protected for purposes of the preparation of the compound of formula 2.

The preferred method for preparing the compounds of the invention is illustrated by the following. syn-7-[2-(2-Aminoxazole-4-yl)-2-methoxyiminoacetamido]-3-acetoxymethyl-3-cephem-4-carboxylic acid is suspended in chloroform and is silylated with monotrimethylsilyltrifluoroacetamide (MSTFA) or other silylating agent. After silylation is complete a solution of the silylated derivative is obtained. To the solution is added an excess of a trialkylsilyliodide such as trimethylsilyliodide and the mixture is agitated until the reaction is completed. The 3-iodomethyl derivative need not be isolated and, preferably, is used as the silylated derivative in the next step of the synthesis. Accordingly, the reaction mixture containing the silylated 3-iodomethyl derivative is evaporated to remove the volatiles, such as the solvent, and the concentrate dissolved in acetonitrile. Tetrahydrofuran is added to the solution which is then stirred for about 5 to 15 minutes. The treatment of the silylated 3-iodomethyl derivative with THF degrades any excess silyl iodide present in the mixture. This removal of excess silyl iodide enhances the recovery and purity of the isoquinolinium final product.

The solution of the silylated 3-iodomethyl derivative is mixed with the isoquinoline or substituted isoquinoline or a solution of either in a solvent such as acetonitrile. The reaction to form the betaine occurs readily at room temperature with stirring. After the reaction is complete, water is added to the mixture to hydrolyze the silyl protecting groups. Following the hydrolysis the betaine product precipitates and is separated by filtration, centrifugation, or other separatory means. The product, if crude at this stage, can be purified by high performance liquid chromatography such as by reverse phase C₁₈ silica chromatography using a suitable solvent system such as acetonitrile/acetic acid/water containing approximately 2% acetic acid and between about 10% and about 20% acetonitrile.

The compounds of the invention can be prepared alternatively by acylation of a 7-amino-3-isoquinolinium-1-ylmethyl (or substituted isoquinolinium-1-ylmethyl)-3-cephem-4-carboxylate. The 3'-quaternary ammonium substituted nucleus compounds are prepared by reacting 7-aminocephalosporanic acid or a silylated derivative thereof with isoquinoline or a substituted isoquinoline. The substituted nucleus is then acylated with an oximino-substituted derivative of the desired amino-substituted heterocyclic acetic acid represented by the formula

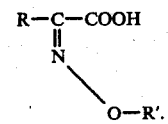

An active derivative of the oximino acetic acid is used in the acylation. For example, the acid group is reacted with hydroxybenzotriazole (HBT) and a carbodiimide such as dicyclohexylcarbodiimide, and the HBT ester used to acylate the 7-amino group of the nucleus. Other active derivatives such as the acid azide, or the anhydride formed with methyl chloroformate or isobutyl chloroformate, can be used for acylation.

The compounds of the invention can be prepared by another alternative procedure comprising the displacement of the acetoxy group of the desired 7-acylamino-3-acetoxymethyl cephalosporin with isoquinoline or substituted isoquinoline. The reaction is illustrated as follows.

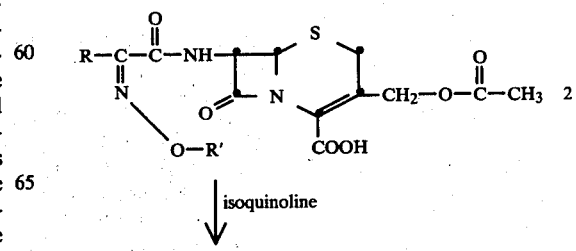

↓ isoquinoline

-continued

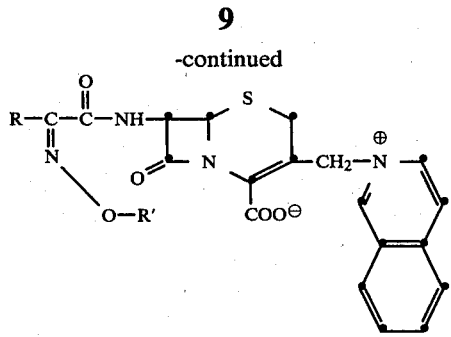

The reaction is carried out in an aqueous solvent system of water and a water miscible organic solvent such as acetone, DMF, DMAC or other suitable solvent at a temperature between about 20° C. and about 55° C. A small amount of an alkali metal iodide such as sodium iodide is added to the reaction mixture to enhance the reaction rate and yield of the reaction.

The 7-[2-(amino-substituted oxazole and 7-[5-(amino-substituted-(1,2,4)-oxadiazole)-2-oximinoacetamido]-3-acetoxymethyl-3-cephem-4-carboxylic acids represented by the formula 2, are prepared by the methods described by Wheeler in copending applications Ser. Nos. 300,140 and 300,159, filed this even date. As described therein, the 7-[2-(2-aminooxazol-4-yl)-2-oximinoacetamido]-3-acetoxymethyl-3-cephem-4-carboxylic acid and the 7-[2-(5-amino-1,2,4-oxadiazol-3-yl)-2-oximinoacetamido]-3-acetoxymethyl-3-cephem-4-carboxylic acid are prepared by the acylation of an ester of 7-aminocephalosporanic acid with the 2-(2-aminooxazol-4-yl)-2-oximinoacetic acid and the 2-(5-amino-1,2,4-oxadiazol-3-yl)-2-oximinoacetic acid, respectively.

The 2-(5-amino-1,2,4-oxadiazol-3-yl)-2-oximinoacetic acid is prepared by reacting an ethyl 2-oximinocyano acetate represented by the formula

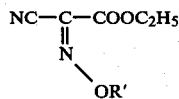

wherein R' is other than hydrogen, with hydroxylamine to obtain a 2-ethoxycarbonyl-2-oximinoacetoxime amide represented by the formula

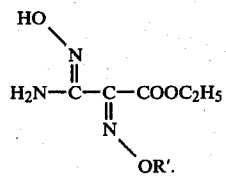

The latter on reaction with trichloroacetyl chloride affords the cyclization product, an ethyl 2-(5-trichloromethyl-1,2,4-oxadiazol-3-yl)-2-oximinoacetate, represented by the formula

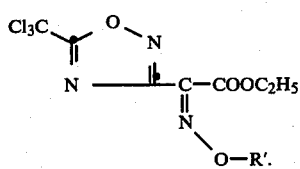

Upon reaction with ammonia the trichloromethyl substituent is replaced with the amino group to provide the 5-aminooxadiazole derivative represented by the formula

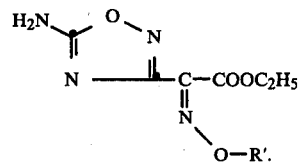

The oximino group of the trichloromethyl substituted oxadiazole is in both the syn and anti forms. During the amminolysis reaction the anti (E) compound forms the amide, 2-(5-amino-1,2,4-oxadiazol-3-yl)-2-oximinoacetamide, while the syn (Z) compound does not. Owing to its lower solubility the anti-amide is readily separated from the syn ester. The syn ethyl 2-(5-amino-1,2,4-oxadiazol-3-yl)-2-oximinoacetate is saponified in aqueous ethanolic sodium hydroxide to sodium syn-2-(5-amino-1,2,4-oxadiazol-3-yl)-2-oximinoacetate and the free acid obtained with the salt by treating the salt with hydrochloric acid.

The compounds represented by the formula 1 wherein R' is hydrogen are prepared by the above reaction sequence wherein the hydroxy group of the oxime is protected during the synthesis of the aminooxadiazole-oximinoacetic acid side chain moiety. For example, the hydroxy group can be protected by a haloacyl group such as mono- or dichloroacetyl, the tetrahydropyranyl group, the 1-methoxyethyl-1-yl group formed with the oxime and methylvinyl ether, or other suitable protecting group. The protection of the free hydroxy group of the oxime function is only necessary through the cyclization step carried out with trichloroacetyl chloride and can be removed thereafter. The free hydroxy group of the oxime need not remain protected during the N-acylation of 7-aminocephalosporanic acid with the oxime-substituted oxadiazole acetic acid.

The compounds represented by the formula 2 wherein R' is a carboxy-substituted alkyl or cycloalkyl group and R" is hydroxy are prepared with the carboxy group protected. The 2-(amino-substituted isoxazole, oxazole or 1,2,4-oxadiazole)-2-oximinoacetic acid ester (formula 2) is alkylated with a halo acid represented by the formula

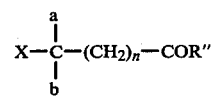

wherein X is chloro, bromo, or iodo and R" is as defined above for formula 1. When R" is hydroxy the carboxy group thus represented is esterified with a carboxy-protecting group eg. as defined hereinabove. Following the base catalyzed alkylation, the carboxy-protecting group is removed.

When R' is an N-substituted carbamoyl group, the heterocyclic free acid wherein R' is hydrogen is acylated with the desired carbamoyl chloride. The carboxy group of the 2-(2-amino-1,2,4-oxadiazol-3-yl)-2-oximinoacetic acid wherein R' is hydrogen is protected with an acid labile ester protecting group, and the oxime group is acylated with the desired carbamoyl chloride e.g. N-methylcarbamoyl chloride, to provide the desired oximino derivative.

The 2-(2-aminooxazol-4-yl)-2-methoximinoacetic acid is prepared by the zinc oxide catalyzed condensation of urea, a γ-bromo-α-methoximinoacetoacetic ester in a suitable organic solvent. Convenient esters are the methyl and ethyl esters. Suitable solvents are the ketones such as acetone, methylethylketone, diethylketone, or methylisobutylketone. The condensation is carried out by suspending zinc oxide in a solution of the urea and the bromoacetoacetic ester in the ketone solvent, and heating the suspension for about 60 hours to about 120 hours. The product is isolated by evaporating the reaction mixture and extracting the product from the concentrate with ethyl acetate. The product is purified by chromatography over alumina.

The 2-(2-aminooxazol-4-yl)-2-methoxyiminoacetic acid is prepared by the saponification of the above ester wherein the 2-amino group is protected. For example, ethyl 2-(2-aminooxazol-4-yl)-2-methoxyiminoacetate is reacted in dimethylacetamide with chloroacetyl chloride in the presence of an acid-binding agent such as a tertiary amine, e.g., triethylamine, to form the amino-protected derivative, 2-[2-(2-chloroacetamido)oxazol-4-yl]-2-methoxyiminoacetate. The latter is then deesterified with aqueous sodium hydroxide to sodium 2-(2-aminooxazol-4-yl)-2-methoxyiminoacetate. Upon acidification, the free acid is obtained. During the saponification the amino-protecting chloroacetyl group is likewise removed.

The above-described preparation of the 2-aminooxazole oximino acid is illustrated by the following reaction scheme.

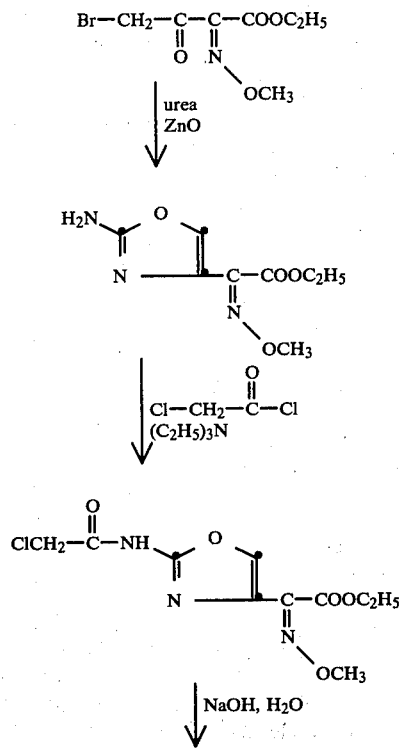

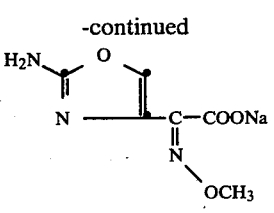

The compounds of the formula 2 are prepared by acylating 7-aminocephalosporanic acid as illustrated by the following reaction scheme.

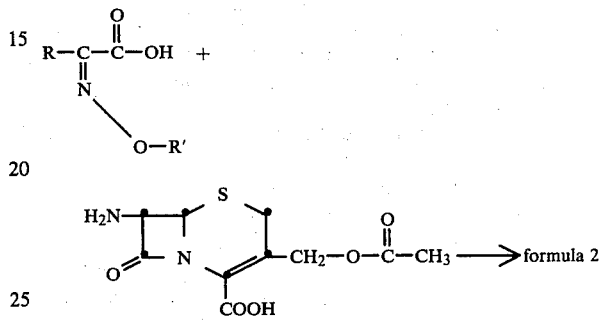

The acylation is preferably carried out with an active derivative of the oximino-substituted acid, for example with an acid halide, acid azide, or an ester. Active esters formed with ethyl chloroformate or isobutyl chloroformate, or with hydroxybenzotriazole (HBT) are suitable in the acylation. The acylation can be carried out in an aqueous or a non-aqueous medium. For non-aqueous acylation, a silylated derivative of 7-ACA such as the trimethylsilyl ester derivative which is substantially soluble in organic solvents is employed. When an acid halide is used as the active carboxylic acid derivative, a hydrogen halide acceptor is also used. Acid acceptors such as the tertiary amines such as triethylamine and pyridine are suitable for use in the acylation. Following the acylation, the silyl ester group is hydrolyzed to the free acid form of the compound of formula 1.

Acylation under aqueous conditions can be carried out using the active ester formed with HBT or alternatively with the acid halide in the presence of an acid binding agent such as a tertiary amine or an alkali metal carbamate or bicarbonate eg. sodium carbonate.

The aqueous acylation with an acid halide can be carried out in an aqueous solvent system comprising a water miscible solvent such as acetone. Solvent suitable for the non-aqueous acylation include tetrahydrofuran, acetonitrile, methylene chloride or other suitable solvent.

Also for purposes of the acylation, the amino group of the heterocyclic ring in the 7-position side chain may be protected. A conventional amino-protecting group can be used, for example, trityl; an alkoxycarbonyl or arylalkoxycarbonyl group such as t-butyloxycarbonyl, t-amyloxycarbonyl, benzyloxycarbonyl, p-nitrobenzyloxycarbonyl, 2,2,2-trichloroethoxycarbonyl, and like groups; an acyl group such as chloroacetyl, dichloroacetyl, and the like. Preferably, the amino group is protected by silylation, for example with a trialkylsilyl group such as trimethylsilyl. It is mentioned, however, that the 5-amino group of the 5-amino-1,2,4-thiadiazol-3-yl group is weakly basic and need not be protected as described above.

Examples of compounds of the invention represented by the formula 1 are described below wherein R, R', and $R_2$ refer to formula 1 above.

![structure: R-C(=NOR')-C(=O)-NH-[cephem]-CH2-N+(isoquinolinium-R2), COO-]

| R* | R' | $R_2$ |
|---|---|---|
| 2-AO | CH₃ | H |
| " | " | 4-Cl |
| " | " | 4-NH₂ |
| " | " | 5-NH₂ |
| " | CH₂COOC₂H₅ | 4-CONH₂ |
| " | CH₃ | 5-OH |
| " | H | 4-OH |
| " | " | 8-OH |
| " | —C(CH₃)₂COOH | H |
| 5-AIO | H | H |
| " | CH₃ | H |
| " | " | 4-NH₂ |
| " | CH₂COOCH₃ | 5-NH₂ |
| " | CH₃ | 4-CONH₂ |
| " | C₂H₅ | 6-Cl |
| 5-AOD | H | H |
| " | CH₃ | H |
| " | " | 5-Cl |
| " | " | 4-NH₂ |
| " | " | 8-OH |
| " | " | 6-OCH₃ |
| " | " | 5-CH₃ |
| " | —CH₂COOH | 4-CONH₂ |
| " | —C(CH₃)₂COOH | H |
| " | —C(O)NHCH₃ | H |

*2-AO is 2-aminooxazol-4-yl; 5-AIO is 5-aminoisoxazol-3-yl; 5-AOD is 5-amino-1,2,4-oxadiazol-3-yl.

A preferred group of compounds of the invention are represented by the formula 1 wherein $R_1$ is isoquinolinium. Another preferred group are represented by the formula 1 wherein $R_1$ is an hydroxy-substituted isoquinolinium group or an amino-substituted isoquinolinium group.

The compounds described herein are oximes and O-substituted oximes which can exist in either the syn or anti forms or as mixtures of both. Whereas both forms are broad spectrum antibiotics, the compound in the syn form generally possess greater activity. Accordingly, the syn compounds are preferred compounds of the invention and are obtained by acylating 7-aminocephalsoporanic acid with a syn 2-(amino-substituted oxazole, isoxazole, or 1,2,4-oxadiazole)-2-oximinoacetic acid and thereafter preparing a compound of the invention as described herein.

Examples of preferred compounds are syn 7-[2-(2-aminooxazol-4-yl)-2-methoxyiminoacetamido]-3-(isoquinolinium-2-ylmethyl)-3-cephem-4-carboxylate, syn 7-[2-(5-amino-1,2,4-oxadiazol-3-yl)-2-methoxyiminoacetamido]-3-(isoquinolinium-2-ylmethyl)-3-cephem-4-carboxylate, syn 7-[2-(5-aminoisoxazol-3-yl)-2-methoxyiminoacetamido]-3-(isoquinolinium-1-ylmethyl)-3-cephem-4-carboxylate, syn 7-[2-(2-aminooxazol-4-yl)-2-methoxyiminoacetamido]-3-(4-hydroxyisoquinolinium-2-ylmethyl)-3-cephem-4-carboxylate, and syn 7-[2-(5-amino-1,2,4-oxadiazol-3-yl)-2-methoxyiminoacetamido]-3-(5-aminoisoquinolinium-2-ylmethyl)-3-cephem-4-carboxylate.

The compounds of the invention form acid addition salts. Salts can be formed with acids such as hydrochloric acid, hydrobromic acid, sulfuric acid, phosphoric acid, and the sulfonic acids such as methanesulfonic acid, and toluenesulfonic acid. These salts of the compounds are depicted by the following partial structural formula

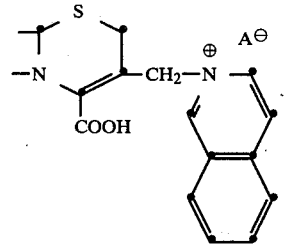

wherein $A^{\ominus}$ is the anion of the acid forming the salt. Also, when in the formula 1 the isoquinolinium group is substituted with a basic amino group or alkylated amino group, the diacid addition salts can be prepared, for example the dihydrochloride salt. The compounds of the invention wherein R" is hydroxy and $R_2$ is an acidic carboxy or sulfo group form salts such as the sodium and potassium salts with suitable bases such as sodium carbonate and potassium carbonate. Salts also can be formed with ammonia and suitable organic amines such as ethanolamine, diethanolamine, diethylamine, procaine, or abietylamine. The salts of the compounds of the invention formed with pharmaceutically acceptable acids and bases are useful forms of the antibiotics for formulating the antibiotics for administration.

The compounds of the formula 1 and the pharmaceutically acceptable non-toxic salts thereof are broad spectrum antibiotics which are particularly effective in inhibiting the growth of gram-negative microorganisms pathogenic to man and animals. For example, the compounds are effective against various pseudomonas, hemophilus, proteus, enterobacter, shigella, salmonella, and other gram-negative microorganisms. The 7-acylamino cephalosporin antibiotics of the formula 1 are also effective against streptococcus and staphylococcus organisms including the penicillin-resistant staphylococci.

The antibiotics of formula 1 and the salts thereof are relatively non-toxic. For example, they either lack or display a low order of nephrotoxicity in in vitro tests.

The antibiotic compounds and the pharmaceutically acceptable non-toxic salts thereof represented by the formula 1 wherein R" is other than a protected carboxy group can be formulated into antibiotic formulations suitable for administration in the treatment of infectious diseases. In one aspect of this invention there is provided an antibiotic formulation comprising the compound of formula 1 or a pharmaceutically acceptable non-toxic salt thereof and a pharmaceutical carrier. The antibiotic or preferably a pharmaceutically acceptable salt thereof can be formulated into formulations suitable for parenteral administration i.e. via the i.v., i.m., or s.c.

routes. For intravenous use the antibiotic can be formulated with one of the commonly employed intravenous fluids and administered by infusion. Such fluids as for example, physiological saline, Ringer's solution, or 5% dextrose can be used.

For intramuscular or intravenous use, the antibiotic can be made up in dosage unit formulations comprising the antibiotic in solid form in sterile vials or ampoules containing from about 100 mg to about 2 g per vial or ampoule. Such unit dosages upon dissolution in a suitable diluent such as Water-for-Injection, 5% dextrose, 5% glucose, or other diluent, are administered to the patient with a syringe.

The antibiotic compounds of the invention may also be formulated into antiseptic solutions for topical use such as for the treatment and prevention of skin infections. Antibacterial solutions containing the antibiotic or an acceptable non-toxic salt thereof containing the antibiotic at a concentration between about one percent and about twenty five percent may be prepared in an aqueous or non-aqueous diluent. Such diluents as water, ethyl alcohol, mixtures of the former, propylene glycol and like diluents can be used. Solubilizing agents, surfactants, preservatives, stabilizing agents, and coloring agents may be added to such solutions as is well known in the art.

In a further aspect of this invention there is provided a method for the treatment of infectious diseases in mammals which comprises administering to said mammal at a dose between about 100 mg and about 2 g a compound represented by the formula 1 or a pharmaceutically acceptable non-toxic salt thereof.

In practicing the above method, the antibiotic can be administered in a single daily dose or in multiple doses per day. The treatment regime may require administration over extended periods of time, e.g. for several days or for two to three weeks. The amount per administered dose or the total amount administered will depend on such factors as the nature and severity of the infection, the age and general health of the patient, and the tolerance of the patient to the antibiotic.

A convenient method of practicing the treatment method is to administer the antibiotic via i.v. infusion. In this procedure, the antibiotic is incorporated in a solution of a physiological fluid, such as 5% dextrose, and the solution infused slowly i.v. Alternatively, the piggyback method of i.v. infusion can also be employed.

The following Preparations and Examples further illustrate the invention. The abbreviations used in the Preparations and Examples have the following meanings: HPLC is high performance liquid chromatography; E refers to the anti form of the oxime; Z refers to the syn form of the oxime; DMSO/$d_6$ is deuterated dimethylsulfoxide; acetone/$d_6$ is deuterated acetone; n.m.r. is nuclear magnetic resonance spectrum; the letters used to characterize the signals in the n.m.r. spectra refer to the following: s is singlet; d is doublet; q is quartet; m is multiplet; J is the coupling constant in Hertz; br s is broad singlet; and t is triplet.

PREPARATION 1

Preparation of
2-[(5-amino-1,2,4-oxadiazol)-3-yl]-2-methoxyimino acetic acid

Step A

Preparation of
2-ethoxycarbonyl-2-methoximinoacetoxime amide

Ethyl 2-methoxyiminocyanoacetate (8 g., 51.2 mmol) was dissolved in ethanol (2B, 20 ml) and the solution was added dropwise to a mixture of hydroxylamine hydrochloride salt (3.56 g, 51.2 mmol) and sodium carbonate (2.72 g, 25.6 mmol) in 3:2 v:v ethanol/water mixture (25 ml). After the addition was complete, the mixture was stirred and heated at the reflux temperature for approximately sixteen hours. The ethanol was then removed in vacuo and the remaining mixture was further diluted with water and then extracted with ethyl acetate. The ethyl acetate layer was washed with water (3×), dried over magnesium sulfate, filtered and concentrated to an oil in vacuo. The resultant oil later crystallized and was recrystallized from ethanol (2B) to yield 750 mg of the product, 2-ethoxycarbonyl-2-methoximinoacetoxime amide: n.m.r. ($d_6$-DMSO) δ0.82 (t, 3, C$\underline{H}_3$CH$_2$), 3.5 (s, 3, OC$\underline{H}_3$), 3.62 (q, 2, CH$_3$C$\underline{H}_2$—), 5.0 (br s, 2, —N$\underline{H}_2$), 10.15 (s, 1, =NO$\underline{H}$).

Step B

Preparation of ethyl
2-[(5-trichloromethyl-1,2,4-oxadiazol)-3-yl]-2-methoxyimino acetate 2-Ethoxycarbonyl-2-methoximinoacetoxime amide (7.65 g, 40 mmol) and pyridine (5 ml, 45 mmol) were dissolved in dioxane (25 ml) and the solution cooled to 10° C. While stirring this solution trichloroacetyl chloride (5 ml, 45 mmol) was added dropwise. The mixture was then allowed to warm to room temperature and the stirring was continued for approximately sixteen hours. The mixture was filtered to remove the pyridine hydrochloride and the filtrate was evaporated to dryness.

The residue was triturated with ether and decanted. The ether layer was washed with a saturated aqueous solution of sodium bicarbonate (2×) and then with water (2×), dried over magnesium sulfate, filtered and concentrated. The solid mass remaining was triturated with hexane and decanted. The remaining solid, which was unreacted starting material, was recrystallized from methanol. The hexane solution from the above decantation was evaporated to yield the product compound, ethyl 2-[(5-trichloromethyl-1,2,4-oxadiazol)-3-yl]-2-methoxyimino acetate: (isomeric mixture)mass spectrum: M+ 315.

Step C

Preparation of ethyl
2-[(5-amino-1,2,4-oxadiazol)-3-yl]-2-Z-methoximinoacetate

Ethyl 2-[(5-trichloromethyl-1,2,4-oxadiazol)-3-yl]-2-methoximinoacetate (7.62 g) was dissolved in ether (40 ml) and the solution added dropwise to anhydrous ammonia (250 ml) with stirring. Stirring was continued while the ammonia evaporated overnight. The residue was triturated thoroughly with ether. Filtration yielded 1.1 g of the undesired 2-[(5-amino-1,2,4-oxadiazol)-3-yl]-2-E-methoximinoacetamide. The filtrate from above was concentrated in vacuo then recrystallized from 2B ethanol to give 2.2 g of the crude title product.

The crude product was combined with ethyl 2-[(5-amino-1,2,4-oxadiazol)-3-yl]-2-methoximinoacetate (0.83 g) made in a previous experiment analogous to the instant procedure. This mixture was dissolved partially in methylene chloride and filtered. The filtrate was chilled to −40° overnight then filtered again. The filtrate was evaporated to dryness and the residue was crystallized from 2B ethanol, yielding 0.209 g of crystals of the title product. The mother liquor of this crystallization was concentrated and the residue was also recrystallized from 2B ethanol, yielding 0.270 g of the title product. Combination of the yields of these two recrystallizations gave 0.479 g of the desired pure product, ethyl 2-[(5-amino-1,2,4-oxadiazol)-3-yl]-2-Z-methoximinoacetate: n.m.r. (solvent) δ1.15 (t, 3, $CH_3$—$CH_2$—O—), 3.95 (s, 3, $CH_3O$—N) 4.25 (q, 2, $CH_3$—$CH_2$—O), 8.05 (br s, 2, $NH_2$); i.r. (mull) in cm.$^{-1}$, 3420 (NH), 1730 ($CO_2Et$), 1670; u.v. (methyl alcohol) λ=227 nm, ε=11,335.

Step D

Preparation of sodium 2-[(5-amino-1,2,4-oxadiazol)-3-yl]-2-Z-methoximinoacetate

Ethyl 2-[(5-amino-1,2,4-oxadiazol)-3-yl]-2-Z-methoximinoacetate (4.28 g, 20 mmol) was dissolved in 2B ethanol (50 ml), followed by addition of 5 N sodium hydroxide solution (4 ml). This reaction mixture was stirred for 0.75 hour at room temperature, then filtered. The solid collected was washed with 2B ethanol and ether to yield 3.43 g (82% yield) of cream-colored crystals of sodium 2-[(5-amino-1,2,4-oxadiazol)-3-yl]-2-Z-methoximinoacetate: i.r. (KBr) 1680, 1665, 1615; u.v. (methanol) $\lambda_{max}$=233, E=10,391;

Analysis: Calculated for $C_5H_5N_4O_4Na$: C, 28.86; H, 2.42; N, 26.92; Found: C, 27.37; H, 2.91; N, 23.91.

Step E

Preparation of 2-[(5-amino-1,2,4-oxadiazol)-3-yl]-2-Z-methoximinoacetic acid

Sodium 2-[(5-amino-1,2,4-oxadiazol)-3-yl]-2-Z-methoximinoacetate (1.0 g) was suspended in ethyl acetate and 1 N hydrochloric acid was added dropwise (6 ml). The layers were separated and the aqueous layer was rewashed with ethyl acetate. The ethyl acetate layers were combined, dried over magnesium sulfate, filtered and the filtrate was evaporated to yield 0.75 g. of 2-[(5-amino-1,2,4-oxadiazol)-3-yl]-2-Z-methoximinoacetic acid NMR ($CDCl_3$): δ4.0 (s, 3, N—$OCH_3$), 7.05 (s, 2, $NH_2$), 8.5 (s, 1, $CO_2H$), (DMSO/$d_6$) δ3.75 (s, 3, N—OMe), 8.12 (s, 2, $NH_2$).

PREPARATION 2

Preparation of benzhydryl 7β-[2-[(5-amino-1,2,4-oxadiazol)-3-yl]-2-Z-methoximinoacetamido]-3-acetoxymethyl-3-cephem-4-carboxylate 2-[(5-Amino-1,2,4-oxadiazol-3-yl]-2-Z-methoximinoacetic acid (0.75 g, 4 mmol) was dissolved in a 1:1 v:v tetrahydrofuran/acetonitrile solvent (20 ml). This solution was stirred as dicyclohexylcarbodiimide (0.5 g, 2.4 mmol), dissolved in the same THF/acetonitrile solvent as above (10 ml), and was added dropwise. The resultant mixture was stirred for 0.5 hour, during which time the dicyclohexylurea precipitated. Benzhydryl 7β-amino-3-acetoxymethyl-3-cephem-4-carboxylate (0.876 g, 2.0 mmol) was added to the solution and stirring was continued for 56 hours. The dicyclohexylurea was collected by filtration and the filtrate was evaporated, triturated with ether and decanted (2×). The ether-insoluble material was dissolved in ethyl acetate, washed with 1 N hydrochloric acid (2×), aqueous sodium bicarbonate solution (2×), and saturated sodium chloride solution (2×). This solution was then dried over magnesium sulfate, filtered and concentrated in vacuo. The resultant material was again triturated with ether and filtered, yielding 0.640 g of crude material. This material was purified by dry silica gel column chromatography, collecting 25 ml fractions. A 1:1 v:v ethyl acetate/cyclohexane used as the eluant for the first 25 fractions, followed by elution with a 3:1 v:v ethyl acetate/cyclohexane solvent. Fractions 33 through 42 were combined, evaporated to dryness, dissolved in chloroform and precipitated from the chloroform by the addition of hexane. The precipitate was collected by filtration, washed with ether then dried in vacuo, yielding 0.420 g of benzhydryl 7β-[2-[(5-amino-1,2,4-oxadiazol)-3-yl]-2-Z-methoximinoacetamido]-3-acetoxymethyl-3-cephem-4-carboxylate: n.m.r. ($CDCl_3$) δ1.90 (s, 3, 3'—OAc), 3.27, 3.55 (ABq, J=6, 2, $C_2$-methylene proton), 4.68, 4.95 (ABq, J=5, 2, $C_3$-methine proton), 4.96 (d, J=1.5, 1, C-6 proton), 5.95 (dd, (J=1.5, 3), 1, C-7 proton), 6.25, (br, s, 2, $NH_2$), 6.85 (s, 1, $CHPh_2$), 7.20 (s, 10, aromatic protons), 8.72 (d, J=3, 1, 7-amido proton).

PREPARATION 3

Preparation of 7β-[2-(5-amino-1,2,4-oxadiazol)-3-yl-2-Z-methoximinoacetamido]-3-acetoxymethyl-3-cephem-4-carboxylic acid Benzhydryl 7β-[2-(5-amino-1,2,4-oxadiazol)-3-yl-2-Z-methoximinoacetamido]-3-acetoxymethyl-3-cephem-4-carboxylate (0.435 g) was dissolved in a formic acid solution (12 ml, 97–100%) containing triethylsilane (0.3 ml) and stirred for 3 hours. The solution was evaporated to dryness, the residue dissolved in ethyl acetate and extracted with 10% aqueous sodium bicarbonate. The sodium bicarbonate solution was washed with ethyl acetate, then layered with ethyl acetate and the resultant solution was acidified to pH 2 with 1 N hydrochloric acid. The ethyl acetate layer was separated and was washed with saturated sodium chloride solution, dried over magnesium sulfate and filtered. The filtrate was concentrated in vacuo and the residue triturated with ether and filtered to yield 0.215 g of the product compound 7β-[2-[(5-amino-1,2,4-oxadiazol)-3-yl-2-Z-methoximinoacetamido]-3-yl-2-Z-methoximinoacetamido]-3-acetoxymethyl-3-cephem-4-carboxylic acid: n.m.r. (acetone/$d_6$) δ1.7 (s, 3, OAc), 3.15, 3.42 (ABq, (J=6), 2, C-2 methylene protons), 3.67 (s, 3, N—$OCH_3$), 4.57, 4.8 (ABq, (J=5), 2, C-3 methylene proton), 4.87 (d, (J=2), 1, C-6 proton), 5.65 (dd, (J=2, 2.5), 1, C-7 protons), 7.05 (br, s, 2, —$NH_2$), 8.25 (d, J=2.5, 1, 7-amido proton).

PREPARATION 4

2-(2-Aminooxazol-4-yl)-2-Z-methoxyiminoacetic acid

Ethyl-δ-bromo-α-methoximinoacetoacetate (100 g, 0.397 mmol), and urea (91 g, 1.98 mmol), were dissolved in methylethylketone (3 l) and zinc oxide (16 g, 0.198 mmol) was added. The suspension was stirred under reflux for 48 hours and was then allowed to cool. The solution was filtered and concentrated in vacuo. The dark residue was dissolved in ethyl acetate and the solution filtered. The filtrate was evaporated in vacuo and the residue was chromatographed over activity III neutral alumina. The column was eluted sequentially with neat cyclohexane (1000 ml), 1:9 v:v ethyl acetate:cyclohexane (1000 ml), 2.8 v:v ethyl acetate:cyclohexane (2000 ml), 3:7 v:v ethyl acetate:cyclohexane (500 ml), and finally with 1:1 v:v ethyl acetate:cyclohexane until no more product was eluted. Fifty-five fractions were taken, although fractions 51 through 55 were 500 ml or greater. The crude product was contained in fractions 51, 52, and 53. The three fractions were evaporated to give a semi-crystalline mass, each of which were triturated with ether and filtered to yield 3 pure crops of crystals of product. These crops of crystals were combined with a second crop of crystals obtained from fraction 52 to yield 8.9 g of ethyl 2-[2-aminooxazol-4-yl]-2-Z-methoximinoacetate.

A mixture of ethyl 2-[2-aminooxazol-4-yl]-2-Z-methoximinoacetate (2.13 g, 10 mmol), triethylamine (1.53 ml, 11 mmol) and dimethylacetamide (25 ml) were chilled to 0° C. by means of an ice bath. A chilled solution of chloroacetyl chloride (0.939 ml, 11 mmol) in 10 ml. of dimethylacetamide was added dropwise to the stirred solution. The reaction mixture was stirred for 0.5 hour at 0° C., and for 19 hours at room temperature. The reaction mixture was poured onto ice and the resultant mixture was extracted with ethyl acetate. The ethyl acetate was washed with water, dried over anhydrous magnesium sulfate, filtered and concentrated in vacuo. After evacuating under high vacuum for 24 hours, the residue was triturated with ether and filtered. The mother liquor was evaporated and the residue was recrystallized from carbon tetrachloride to give 0.456 g of ethyl 2-[2-chloroacetamido)oxazol]-4-yl]-2-Z-methoximinoacetate; melting point; 91°–92° C., n.m.r. (CDCl$_3$) $\delta$1.32 (t, 3, —CH$_3$, J=7.5 Hz), 4.0 (s, 3, OCH$_3$), 4.1 (s, 2, Cl—CH$_2$—), 4.37 (q, 2, —O—CH$_2$—, J=7.5 Hz), 7.25 (s, 1, aromatic proton).

Sodium hydroxide (5 N, 2 equivalents plus a 10% excess, 4.6 ml, 22.86 mmol) was added dropwise to a stirred suspension of ethyl 2-[2-(chloroacetamido)oxazol-4-yl]-2-Z-methoximinoacetate (3.0 g, 10.38 mmol) in water (90 ml). Dissolution of the ester was complete within about 15 to 20 minutes, and stirring was continued for an additional hour. The mixture was chilled and acidified by the dropwise addition of 1 N hydrochloric acid (6 ml). The aqueous layer was saturated with sodium chloride and the mixture was extracted with large quantities of ethyl acetate. The ethyl acetate extracts were dried over anhydrous sodium sulfate, filtered, combined and concentrated in vacuo, yielding 0.453 g of 2-(2-aminooxazol-4-yl)-2-Z-methoximinoacetic acid; melting point; 170°–174° C. (decompose), n.m.r. (DMSO/d$_6$) $\delta$3.84 (s, 3, NOCH$_3$), 6.77 (br, s, 2, amino), $\delta$7.48 (s, 1, aromatic proton).

PREPARATION 5

Benzyl 7$\beta$-[2-(2-aminooxazol-4-yl)-2-Z-methoximinoacetamido]-3-acetoxymethyl-3-cephem-4-carboxylate 2-(2-Aminooxazol-4-yl)-2-Z-methoximinoacetic acid (0.261 g, 1 mmol) was dissolved in a mixture of dimethylacetamide (3 ml) and methylene chloride (3 ml). Triethylamine (0.139 ml, 1 mmol) was added to this solution and the resultant mixture was added dropwise to a stirred, chilled solution of iso-butyl-chlorocarbonate in 25 ml of methylene chloride. The reaction mixture was stirred for 1 hour, at the end of which time a methylene chloride (5 ml) solution of benzhydryl 7$\beta$-amino-3-acetoxymethyl-3-cephem-4-carboxylate was added dropwise. Initially, the reaction mixture was stirred at 0° to 10° C. and was allowed to gradually warm to ambient temperature and stirred overnight.

The reaction mixture was evaporated in vacuo and the residue was taken up in ethyl acetate. The ethyl acetate solution was washed sequentially with 1 N hydrochloric acid, 10% aqueous sodium bicarbonate, and a saturated aqueous sodium chloride solution. Removal of the ethyl acetate solvent in vacuo, after drying the solution over sodium sulfate and filtering, resulted in a yellow foam. This crude product mixture was chromatographed over Activity III Silica Gel (100–200 mesh, Woehlm). Elution was begun with 7:3 v:v ethyl acetate:cyclohexane (fractions 1 through 19), then neat ethyl acetate (fractions 20 through 34), and finally 9:1 v:v ethyl acetate:methanol (fractions 34 through 37). The desired product, benzhydryl 7$\beta$-[2-(2-aminooxazol-4-yl)-2-Z-methoximinoacetamido]-3-acetoxymethyl-3-cephem-4-carboxylate, was contained in fractions 14 through 30, and these fractions were combined to yield 0.100 g of the desired product: n.m.r. (CDCl$_3$) $\delta$1.98 (s, 3, methyl of 3-acetoxymethyl), 3,3 and 3.56 (ABq, 2, C-2), 4.75 and 5.01 (ABq, 2, C-3'), 5.02 (d, 1, C-6), 5.25 (br, s, 2, amino), 5.95 (q, 1, C-7), 7.91 (s, 1, benzyl methine proton), 7.3 (m, 11, phenyl rings and oxazole ring), 8.42 (d, 1, amido proton).

PREPARATION 6

7$\beta$-[2-(2-Aminooxazol-4-yl)-2-Z-methoximinoacetamido]-3-acetoxymethyl-3-cephem-4-carboxylic acid Benzyl 7$\beta$-[2-(2-aminooxazol-4-yl)-2-Z-methoximinoacetamido]-3-acetoxymethyl-3-cephem-4-carboxylate (approximately 100 mg, 0.16 mmol) was dissolved in a mixture of formic acid (97–100%, 4 ml) and triethylsilane (0.04 ml, 0.25 mmol). The reaction mixture was stirred at room temperature for 3 hours, was diluted with ethyl acetate, and evaporated to a gum. The gum was treated twice with an ethyl acetate/acetonitrile mixture to give a light brown powder. The powder was further dried by evaporation in vacuo for 1 hour. The brown powder was then dried with ether for 0.5 hour, sonnicated, filtered and airdried to yield 64 mg (91%) of 7$\beta$-[2-(2-aminooxazol-4-yl)-2-Z-methoximinoacetamido]-3-acetoxymethyl-3-cephem-4-carboxylic acid: n.m.r. (DMSO/d$_6$) $\delta$2.0 (s, 3, acetoxymethyl methyl), 3.4 (m, 2, C-2), 3.85 (s, 3, =NOCH$_3$), 4.85 (q, 2, J=16, C-3'), 5.15 (d, 1, J=6, C-6), 5.8 (q, 1, J=4, C-7), 6.85 (s, 2, amino), 7.5 (s, 1, oxazole ring), 9.6 (d, 1, J=9, amido).

PREPARATION 7

7$\beta$-[2-(2-Aminooxazol-4-yl)-2-Z-methoximinoacetamido]-3-acetoxymethyl-3-cephem-4-carboxylic acid A mixture of 1-hydroxybenzotriazole monohydrate (1.02 g, 6.68 mmol) and triethylamine (1.138 ml, 8.16 mmol) in dimethylacetamide (8 ml) was chilled in an ice-acetone bath and a solution of methanesulfonyl chloride (0.57 ml, 7.3 mmol) in 2 ml. of dimethylacetamide was added dropwise. The solution was stirred at 0° to 10° C. for 1.5 hours. A solution of 2-(2-aminooxazol-4-yl)-2-Z-methoximinoacetic acid (1.235 g, 6.68 mmol), in dimethylacetamide (2.5 ml) containing triethylamine (1.01 ml) was then added dropwise to the cold mixture, and the solution was stirred at 0° to 10° C. for an additional 1.5 hours. Water (21 ml) was then added dropwise and within 10 minutes after the water had been added, the product precipitated, was collected by filtration, washed with cold water, and dried in vacuo to yield 1.277 g (63%) of the product, 1-(N-oxide)benzotriazol-3-yl 2-[2-aminooxazol-4-yl]-2-Z-methoximinoacetamide.

7β-Amino-3-acetoxymethyl-3-cephem-4-carboxylic acid (0.43 g, 1.58 mmol) was suspended in 25 ml of a 1:1, v:v water:acetone solvent cooled in an ice bath and triethylamine (0.2 ml, 1.48 mmol) was added dropwise to the stirred solution. After the solution formed, 1-(N-oxide)benzotriazol-3-yl 2-[2-aminooxazol-4-yl]-2-Z-methoximinoacetamide (0.5 g, 11.66 mmol) was added portionwise. The pH of the solution was maintained at approximately 7.5 by the periodic additions of 45% aqueous potassium phosphate solution. After the addition of the benzotriazole amide was complete, the mixture was slowly allowed to warm to room temperature. After approximately 2 hours, dissolution had occurred and the solution was stirred overnight. The acetone was removed, and the aqueous concentrate was diluted with water, layered with ethyl acetate, and the pH of the solution adjusted to pH 2.5 by the addition of 1 N hydrochloric acid. The ethyl acetate layer was then separated, dried, filtered and evaporated in vacuo. The partially crystalline residue was triturated with ether and filtered to yield 0.3 g of 7β-[2-(2-aminooxazol-4-yl)-2-Z-methoxyiminoacetamido]-3-acetoxymethyl-3-cephem-4-carboxylic acid: n.m.r. (DMSO/$d_6$) δ2.0 (s, 3, OAc), 3.32 and 3.61 (ABq, 2, J=18 Hz, C-2 protons), 4.85 (s, 3, OC$\underline{H}_3$), 4.7 and 5.0 (ABq, 2, J=12 Hz, C-3' protons), 5.08 (d, 1, J=4.5 Hz, C-6 proton), 5.72 (q, 1, J=4.5 and 9 Hz, C-7 proton), 6.6 (br, s, 2, amino), 7.38 (s, 1, oxazole aromatic proton), 9.5 (d, 1, J=9 Hz, 7-amido N-proton); u.v. (methanol) λmax=265 ($\epsilon_m$=19,254), λmax=265 ($\epsilon_m$=10,200); Analysis: Calculated: C, 43.74; H, 3.90; N, 15.94. Observed: C, 44.01; H, 3.97; N, 15.75.

EXAMPLE 1 syn-7-[2-(2-Aminooxazol-4-yl)-2-methoxyiminoacetamido]-3-(isoquinolinium-2-ylmethyl)-3-cephem-4-carboxylate A suspension of syn-7-[2-(2-aminooxazol-4-yl)-2-methoxyiminoacetamido]-3-acetoxymethyl-3-cephem-4-carboxylic acid in chloroform is treated at room temperature with excess monotrimethylsilyltrifluoroacetamide and stirred until a solution of the silylated derivative is obtained. Excess trimethylsilyliodide is added to the solution and after the mixture is stirred for 30 minutes, the mixture is evaporated. The residue of the silylated 3-iodomethyl derivative is dissolved in acetonitrile, and the solution treated with tetrahydrofuran in an amount sufficient to scavenge any excess trimethylsilyliodide. After stirring the solution for about 15 minutes, isoquinoline is added in an amount in excess of the stoichiometric amount and the reaction mixture is stirred for about 1 to 2 hours. Sufficient water to hydrolyze the silyl groups is added to the reaction mixture and the product is separated by filtration. The product is purified by $C_{18}$ silica gel reverse phase HPLC.

EXAMPLES 2 THROUGH 10

By following the reaction procedures and conditions used in the preparation described by Example 1, the following compounds of the invention can be prepared with the silylated 3-iodomethyl cephalosporin, having the same 7-acyl side chain as the final product, with the indicated isoquinoline.

EXAMPLE 2 syn-7-[2-(2-Aminooxazol-4-yl)-2-methoxyiminoacetamido]-3-(4-aminoisoquinolinium-2-ylmethyl)-3-cephem-4-carboxylate is prepared with 4-aminoisoquinoline.

EXAMPLE 3 syn-7-[2-(2-Aminooxazol-4-yl)-2-methoxyiminoacetamido]-3-(5-aminoisoquinolinium-2-ylmethyl)-3-cephem-4-carboxylate is prepared with 5-aminoisoquinoline.

EXAMPLE 4 syn-7-[2-(2-Aminooxazol-4-yl)-2-methoxyiminoacetamido]-3-(5-hydroxyisoquinolinium-2-ylmethyl)-3-cephem-4-carboxylate is prepared with 5-hydroxyisoquinoline.

EXAMPLE 5 syn-7-[2-(5-Amino-1,2,4-oxadiazol-3-yl)-2-methoxyiminoacetamido]-3-(isoquinolinium-2-ylmethyl)-3-cephem-4-carboxylate is prepared with isoquinoline.

EXAMPLE 6 syn-7-[2-(5-Amino-1,2,4-oxadiazol-3-yl)-2-methoxyiminoacetamido]-3-(7-aminoisoquinolinium-2-ylmethyl)-3-cephem-4-carboxylate is prepared with 7-aminoisoquinoline.

EXAMPLE 7 syn-7-[2-(5-Amino-1,2,4-oxadiazol-3-yl)-2-methoxyiminoacetamido]-3-(4-hydroxyisoquinolinium-2-ylmethyl)-3-cephem-4-carboxylate is prepared with 4-hydroxyisoquinoline.

EXAMPLE 8 syn-7-[2-(5-Amino-1,2,4-oxadiazol-3-yl)-2-methoxyiminoacetamido]-3-(5-carbamoylisoquinolinium-2-ylmethyl)-3-cephem-4-carboxylate is prepared with 5-carbamoylisoquinoline.

EXAMPLE 9 syn-7-[2-(5-Aminoisoxazol-3-yl)-2-methoxyiminoacetamido]-3-(isoquinolinium-2-ylmethyl)-3-cephem-4-carboxylate is prepared with isoquinoline.

EXAMPLE 10 syn-7-[2-(5-Aminoisoxazol-3-yl)-2-methoxyiminoacetamido]-3-(2-hydroxyisoquinolinium-2-ylmethyl)-3-cephem-4-carboxylate is prepared with 8-hydroxyisoquinoline.

We claim:

1. A compound of the formula

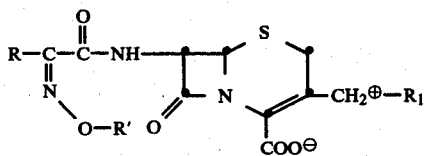

wherein R is an amino-substituted heterocyclic of the formula

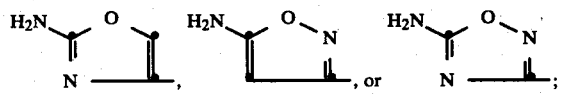

R' is a hydrogen, $C_1-C_4$ alkyl, or a carboxy-substituted alkyl or carboxy-substituted cycloalkyl group of the formula

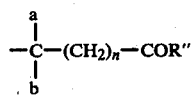

wherein a and b when taken separately are independently hydrogen or $C_1-C_3$ alkyl, and when taken together with the carbon atom to which they are attached form a $C_3-C_7$ carbocyclic ring; R'' is hydroxy, $C_1-C_4$ alkoxy, or amino; or R' is a carbamoyl group of the formula

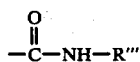

wherein R''' is $C_1-C_3$ alkyl, phenyl, or $C_1-C_3$ alkyl substituted by phenyl; $R_1$ is isoquinolinium or substituted isoquinolinium substituted by amino, $C_1-C_4$ alkylamino, di-($C_1-C_4$ alkyl)amino, hydroxy, $C_1-C_4$ alkoxy, halogen, $C_1-C_4$ alkyl, cyano, trifluoromethyl, sulfo(—$SO_3H$), aminosulfonyl(—$SO_2NH_2$), carboxy, $C_1-C_4$ alkoxycarbonyl, hydroxy substituted $C_1-C_3$ alkyl, formyl, $C_2-C_4$ alkanoyl, thiocarbamoyl, or carbamoyl; and the pharmaceutically acceptable non-toxic salts thereof.

2. The compound of claim 1 wherein $R_1$ is isoquinolinium.

3. The compound of claim 2 wherein R' is $C_1-C_4$ alkyl.

4. The compound of claim 3 wherein R' is methyl.

5. The compound of claim 4 wherein R is 2-aminooxazol-4-yl or 5-amino-1,2,4-oxadiazol-3-yl.

6. The compound of claim 1 wherein $R_1$ is an amino-substituted isoquinolinium group.

7. The compound of claim 6 wherein R' is methyl.

8. The compound of claim 1 wherein $R_1$ is a hydroxy-substituted isoquinolinium group.

9. The compound of claim 8 wherein R' is methyl.

10. A pharmaceutical formulation which comprises a therapeutically effective amount of an antibiotic compound of claim 1 and a pharmaceutically acceptable diluent.

11. The formulation of claim 10 where in said antibiotic compound $R_1$ is isoquinolinium.

12. A method for treating bacterial infections in a mammal which comprises administering in a dose between about 100 mg and about 2 g of an antibiotic compound of claim 1 or a pharmaceutically acceptable salt thereof.

13. The method of claim 12 where in said antibiotic compound $R_1$ is isoquinolinium.

* * * * *